(12) United States Patent
Beyerlein

(10) Patent No.: US 7,106,574 B2
(45) Date of Patent: Sep. 12, 2006

(54) SYSTEMS AND METHODS FOR DETECTING TISSUE CONTACT AND NEEDLE PENETRATION DEPTH

(75) Inventor: Dagmar Beyerlein, San Francisco, CA (US)

(73) Assignee: Advanced Cardiovascular Systems, Inc., Santa Clara, CA (US)

( * ) Notice: Subject to any disclaimer, the term of this patent is extended or adjusted under 35 U.S.C. 154(b) by 0 days.

(21) Appl. No.: 11/211,107

(22) Filed: Aug. 23, 2005

(65) Prior Publication Data
US 2005/0283117 A1   Dec. 22, 2005

Related U.S. Application Data

(62) Division of application No. 10/262,203, filed on Sep. 30, 2002, now Pat. No. 6,951,549.

(51) Int. Cl.
*H01G 4/06* (2006.01)
*A61M 5/00* (2006.01)

(52) U.S. Cl. ......................... 361/313; 604/117
(58) Field of Classification Search ................ 604/116, 604/117, 181, 21; 607/116, 118, 119, 122; 606/32; 361/313; 29/25, 41, 854
See application file for complete search history.

(56) References Cited

U.S. PATENT DOCUMENTS

| | | | | |
|---|---|---|---|---|
| 2,763,935 A | * | 9/1956 | Whaley et al. | 33/511 |
| 4,819,661 A | * | 4/1989 | Heil et al. | 607/127 |
| 5,389,069 A | * | 2/1995 | Weaver | 604/21 |
| 5,484,416 A | * | 1/1996 | Gittings | 604/164.08 |
| 6,102,926 A | * | 8/2000 | Tartaglia et al. | 606/170 |
| 6,298,256 B1 | * | 10/2001 | Meyer | 600/373 |
| 6,309,370 B1 | * | 10/2001 | Haim et al. | 604/66 |
| 6,391,005 B1 | * | 5/2002 | Lum et al. | 604/117 |
| 6,692,492 B1 | * | 2/2004 | Simpson et al. | 606/41 |
| 6,706,016 B1 | * | 3/2004 | Cory et al. | 604/117 |
| 6,709,380 B1 | * | 3/2004 | Green et al. | 600/3 |
| 6,965,791 B1 | * | 11/2005 | Hitchcock et al. | 600/345 |
| 2002/0008526 A1 | * | 1/2002 | Martin et al. | 324/678 |
| 2003/0028094 A1 | * | 2/2003 | Kumar et al. | 600/410 |
| 2003/0120297 A1 | * | 6/2003 | Beyerlein | 606/185 |
| 2004/0260240 A1 | * | 12/2004 | Beyerlein | 604/117 |
| 2005/0004513 A1 | * | 1/2005 | Beyerlein | 604/66 |

OTHER PUBLICATIONS

U.S. Appl. No. 10/166,854.*
U.S. Appl. No. 10/656,491.*
U.S. Appl. No. 10/869,691.*
U.S. Appl. No. 10/029,608.*
U.S. Appl. No. 10/166,854.*
U.S. Appl. No. 10/656,491.*
U.S. Appl. No. 10/869,691.*
U.S. Appl. No. 10/029,608.*

* cited by examiner

*Primary Examiner*—Sharon Kennedy
(74) *Attorney, Agent, or Firm*—Blakely, Sokoloff, Taylor & Zafman LLP

(57) ABSTRACT

A system for detecting tissue contact and penetration depth. The system comprises a needle sheath having a needle sheath inner diameter and a needle sheath outer diameter. A first conductive region is disposed on the needle sheath inner diameter. A needle having a needle insulation layer on the outer diameter upon which a second conductive region is disposed within the first conductive region. A dielectric layer is disposed between the first conductive tube and the second conductive tube. A capacitance sensor is coupled to the first conductive region and the second conductive region.

6 Claims, 10 Drawing Sheets

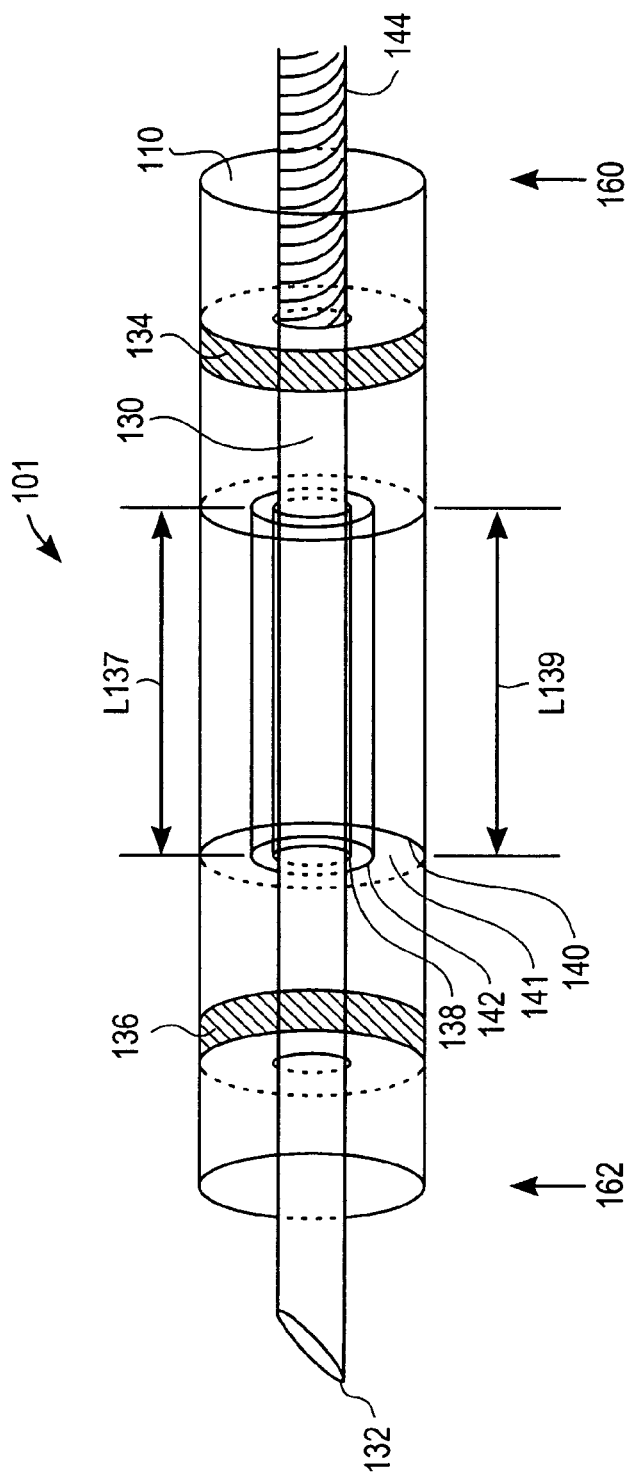
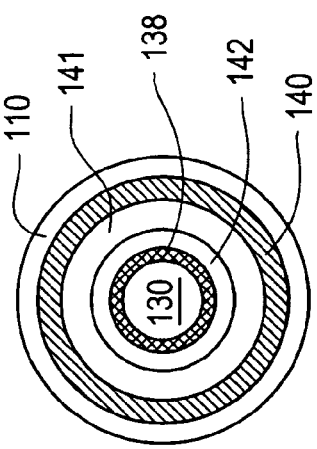
FIG. 3
FIG. 4

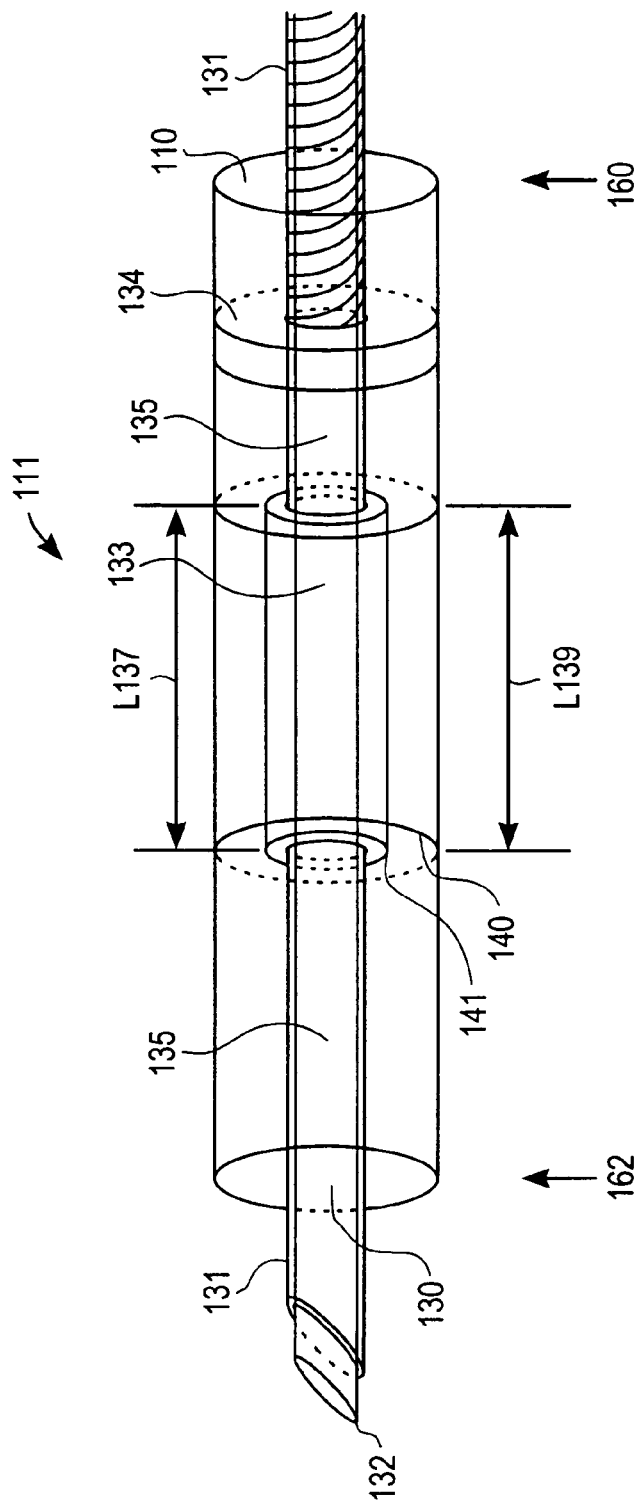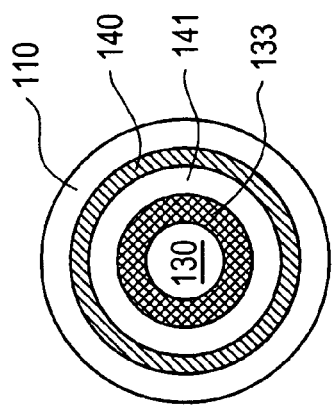
FIG. 5
FIG. 6

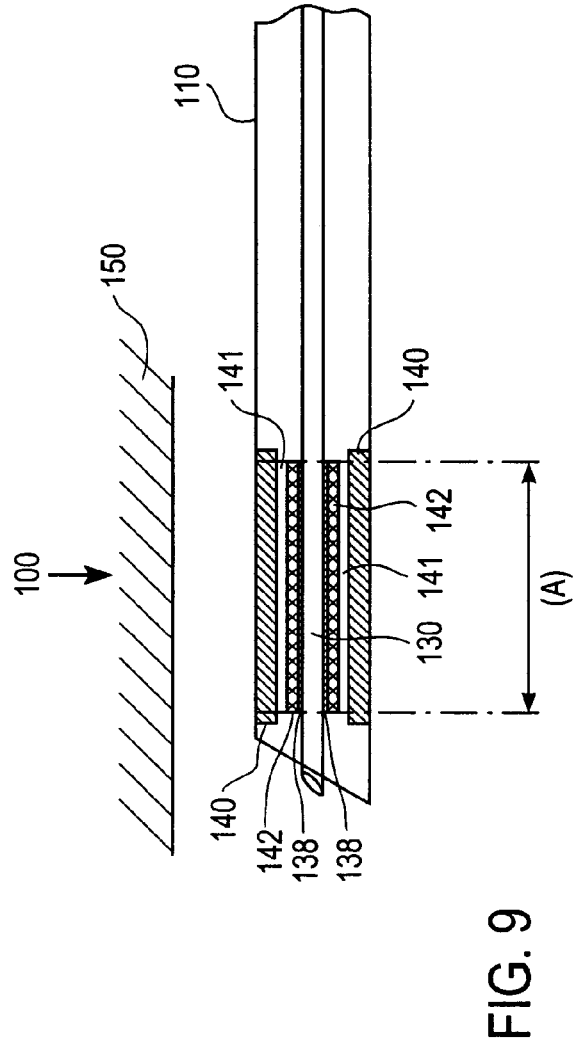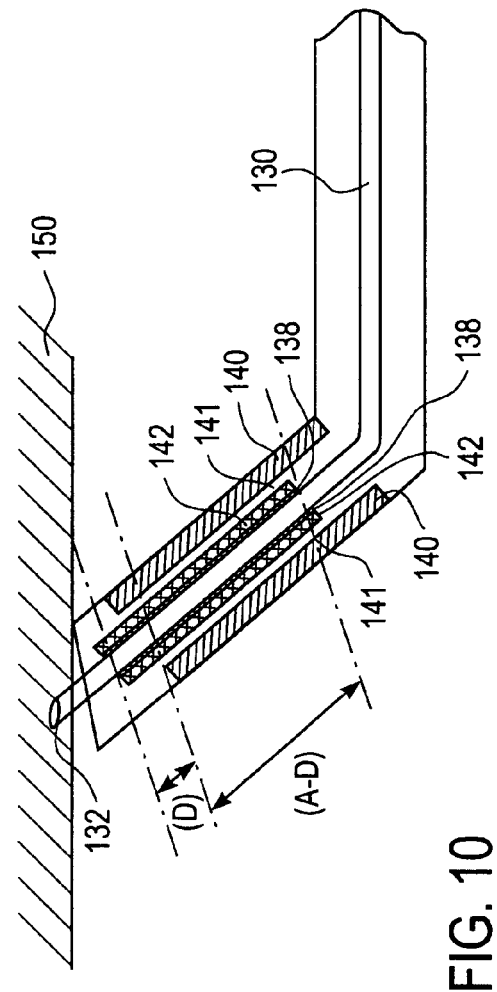
FIG. 9
FIG. 10

SYSTEMS AND METHODS FOR DETECTING TISSUE CONTACT AND NEEDLE PENETRATION DEPTH

This application is a divisional application of U.S. patent application Ser. No. 10/262,203, filed Sep. 30, 2002 now U.S. Pat. No. 6,951,549.

FIELD OF THE INVENTION

The invention relates generally to needles, and more particularly, to a system and method for detecting tissue contact and needle penetration depth.

BACKGROUND

Drug delivery systems currently exist that supply therapeutic substances through a needle to regions of a patient's body. Such regions may include a diseased blood vessel, body cavity or organ. In the case of a diseased blood vessel, for example, the therapeutic agent may be used to treat an arterial lesion and/or to promote an angiogenic response.

In some applications, a needle may be connected to a catheter assembly to deliver the therapeutic agent deep into the body. In this application, it is difficult to determine when the needle contacts the organ, cavity wall, or vessel wall. Further, it is difficult to determine the penetration depth of the needle. In many of the applications for which a needle catheter assembly is used to deliver therapeutic agents to regions within the body, the agent must be delivered to a precise location. Accordingly, it is desirable to provide feedback that indicates when the needle contacts the cavity or vessel wall and when the needle has been inserted to a predetermined depth.

SUMMARY OF THE INVENTION

Systems and methods for determining tissue contact and penetration depth are provided. In one aspect, the system comprises a needle sheath having a needle sheath inner diameter and a needle sheath outer diameter. A first conductive region, such as a first conductive tube, is disposed on the needle sheath inner diameter. A needle having a second conductive region, such as a second conductive tube, is disposed on the needle outer diameter wherein the needle is disposed coaxially within the first conductive region. A dielectric layer is disposed between the first conductive region and the second conductive region. The first and second conductive region, separated by a dielectric, operates as a capacitor. A capacitance sensor is coupled to the first conductive region and the second conductive region.

The first conductive region, the second conductive region, and the dielectric layer form a coaxial capacitive displacement transducer that can detect small changes in capacitance of the coaxial capacitor as the area of the conductive region overlap changes as the needle is advanced or retracted within the needle sheath. The capacitance change is proportional to the distance traveled (e.g., advanced or retracted) by the needle. The present invention can be used to determine the penetration depth of the needle or when the needle contacts a particular target site, e.g., a blood vessel wall.

BRIEF DESCRIPTION OF THE DRAWINGS

The present invention is illustrated by way of example, and not limitation, in the figures of the accompanying drawings in which:

FIG. 3 illustrates an exemplary needle assembly with a capacitor;

FIG. 4 illustrates a cross-sectional view of the needle assembly with a capacitor shown in FIG. 3;

FIG. 5 illustrates another exemplary needle assembly with a capacitor;

FIG. 6 illustrates a cross-sectional view of the needle assembly with the capacitor shown in FIG. 5;

FIGS. 9–10 illustrate the embodiment of a delivery catheter of FIG. 8 in different positions with respect to the tissue;

DETAILED DESCRIPTION

Systems and methods for detecting tissue contact and needle penetration depth are described. In the following detailed description of the present invention, numerous specific details are set forth in order to provide a thorough understanding of the present invention. However, it will be apparent to one skilled in the art that the present invention may be practiced without these specific details. In some instances, well-known structures and devices are shown in block diagram form, rather than in detail, in order to avoid obscuring the present invention. Several exemplary embodiments are described herein, and it will be appreciated that alternative embodiments exist within the scope of this invention.

Figure 1:
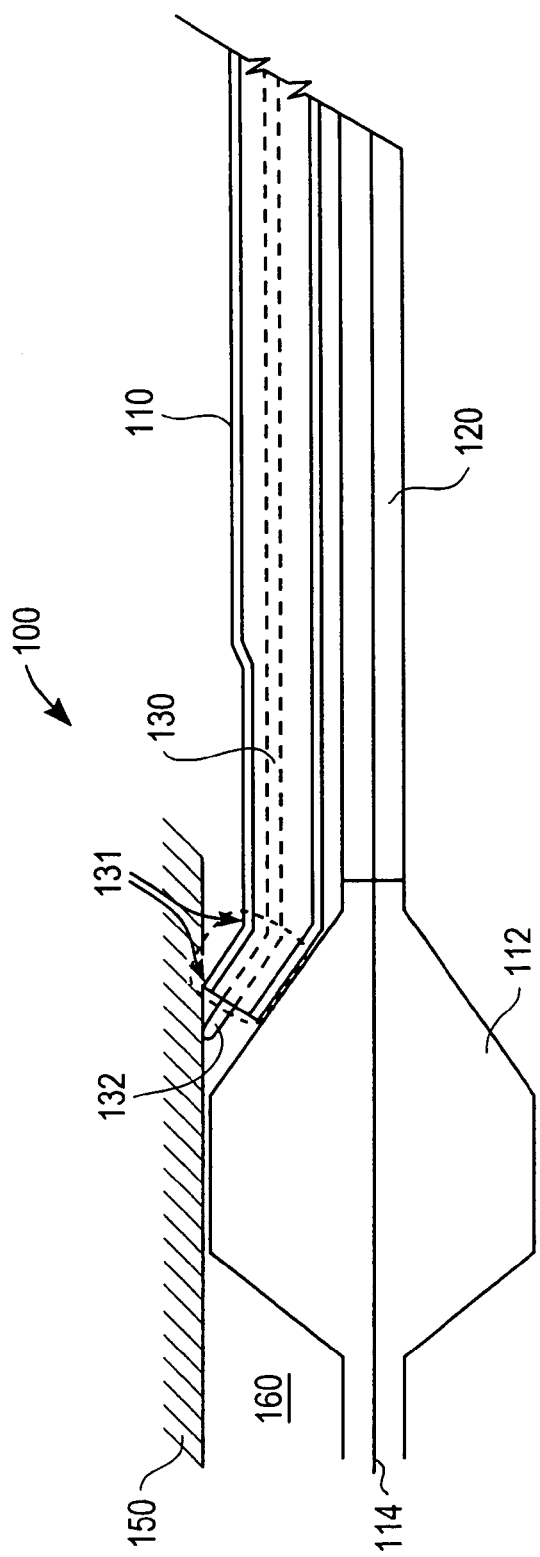
FIG. 1 illustrates a side cross-sectional view of one embodiment of a needle delivery catheter.

FIG. 1 illustrates a side cross sectional view of one embodiment of a delivery catheter 100. The delivery catheter 100 can be used to provide therapeutic agents to a particular region of a patient's body, for example, to prevent or treat arterial disease (e.g. arterial stenosis or restenosis). The delivery catheter 100 can be any medical device designed for insertion into a region of a patient's body to permit injection of therapeutic agents, therapeutic fluids, and the like or to perform other functions (e.g., ablation of tissue or sense parameters of the tissue). It is contemplated that the delivery catheter has applicability for use with any region within a patient's body, including blood vessels (e.g. coronary arteries), urinary tract, intestinal tract, kidney ducts, and the like. The delivery catheter 100 can also be used to extract bodily fluid from a patient's body.

In FIG. 1, the delivery catheter 100 includes a needle 130 within a needle sheath 110. The needle 130 is used for injecting therapeutic agents into a patient's body or to extract bodily fluid from a patient's body or for any other purposes relating to treating a patient. The needle sheath 110 is, in one embodiment, mounted on a dilatation catheter 120, which includes at least one balloon. In other embodiments, the needle sheath 110 is mounted on other types of catheters. The delivery catheter 100 is shown within a cavity 160 of a patient's body as illustrated in FIG. 1. The cavity 160 may be a lumen of a blood vessel, such as a coronary artery. The delivery catheter 100 is maneuvered over a guidewire 114. The guidewire directs the delivery catheter 100 through torturous passageways within the body to arrive at the desired body cavity 160. The catheter 120 has a balloon 112 that inflates and directs the needle tip 132, which is extendable, toward body tissue such as a blood vessel wall 150. An example of an embodiment of the catheter 122 is described in a co-pending U.S. patent application Ser. No. 09/746,498, filed on Dec. 21, 2000, which application is incorporated herein by reference. The various embodiments of the invention may be used other types of catheters.

Figure 2:
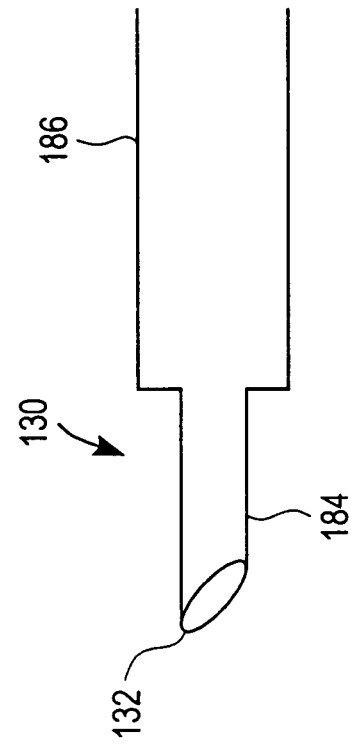
FIG. 2 illustrates an exemplary needle.

FIG. 2 illustrates an enlarged view of an exemplary embodiment of a needle 130 included in the delivery catheter 100 as shown in FIG. 1. Here, the needle 130 has a stepped design with a distal (first) portion 184 and a proximal (second) portion 186. The needle tip 132 is located on the distal portion 184. In one embodiment, the distal portion 184 has a smaller diameter than the proximal portion 186. In one embodiment, the distal portion 184 has an outer diameter of about 0.008 to about 0.26 inches and the proximal portion 186 has an outer diameter of about 0.012 to about 0.3 inches. In another embodiment, the needle 130 has an outer diameter between about 0.008 and 0.3 inches and an inner diameter between about 0.004 and 0.26 inches. In alternative embodiments, these dimensions may change according to the desired use of the needle.

It is difficult to determine when the needle tip 132 contacts the organ, cavity wall, or vessel wall of a patient's body and difficult to determine the penetration depth of the needle 130. In the exemplary embodiments of the present invention, a capacitor is incorporated into the delivery catheter 100. A capacitor is created using two conductive regions, (e.g., two conductive plates, two conductive rings, or two conductive tubes, two conductive cylinders, etc.), separated by an insulation or a dielectric region (e.g., a dielectric layer, a dielectric ring, or a dielectric tube). A capacitor is a device that temporarily stores an electric charge and is used to oppose a change in voltage. Capacitance is determined by the material used as the dielectric region, the area of overlap between the two conductive regions and the distance between the two conductive regions. Capacitance C is measured in farads (F) and is given by the expression $$C = (A\epsilon_0\epsilon_r)/d$$

where A is the area of overlap between the two conductive regions or tubes (m$^2$); $\epsilon_0$ is the permittivity of free space (8.854×10$^{-12}$ F.m$^{-1}$); $\epsilon_r$ is the relative permittivity of the dielectric between the two conductive regions (no unit); and d is the distance between the two conductive regions.

The capacitance can be changed by varying either the area of overlap A, the relative permittivity of the dielectric $\epsilon_r$, or the distance d between the two capacitor plates. In one embodiment, the capacitance is changed by varying the area of capacitor plate overlap A. Varying the area where the two capacitor plates overlap leads to a change in capacitance that can be measured. The change in capacitance is proportional to the change in the areas where the two capacitor plates overlap. For example, as the area of overlap A increases, the capacitance C increases; and, as the area of overlap A decreases, the capacitance C decreases. In one embodiment, the capacitance change is used to provide feedback as to the penetration depth of or the distance traveled by the needle 130 as described below.

In one embodiment, a capacitor 101 is incorporated into a portion 131 of the delivery catheter 100 shown in FIG. 1. FIG. 3 illustrates an exemplary embodiment of the delivery catheter 100 that includes the capacitor 101. The capacitor 101 of the delivery catheter 100 comprises a first conductive tube 140, a second conductive tube 142, and an insulation tube (or a dielectric tube) 141. The first conductive tube 140 and the second conductive tube 142 function as the two conductive regions for the capacitor 101. It will be appreciated that these two conductive tubes are conductive regions which together forms a capacitor, and it will be further appreciated that these regions may have any of a number of different shapes such as tubes, rings, or curved plates which do not form a complete ring or tube around the circumference or the perimeter of the needle or the needle sheath 110.

The first conductive tube 140 and the second conductive tube 142 are made of conductive materials such as aluminum, gold, silver, copper, stainless steel, nitinol, or conductive polymer, to name a few. The first conductive tube 140 and the second conductive tube 142 are oppositely charged. For example, the first conductive tube 140 may be positively charged (+) and the second conductive tube 142 may be negatively charged (−). In order to minimize the profile of the catheter, the first conductive tube 140 and the second conductive tube 142 should be as thin as possible. In one embodiment, each of the first conductive tube 140 and the second conductive tube 142 has a thickness between about 0.001 inches to about 0.25 inches.

In one embodiment, the first conductive tube 140, the second conductive tube 142 and the dielectric tube 141 form a coaxial capacitive displacement transducer that can detect small changes in capacitance of the coaxial capacitor as the area of conductive tube overlap changes as the needle 130 is moved within the needle sheath 110. The coaxial capacitor enables the determination of a capacitance change that is dependent upon the movement of the needle 130 within the needle sheath 110. In one embodiment, the capacitance between the first conductive tube 140, the second conductive tube 142 changes as the needle 130 is advanced toward a target site, for example, the blood vessel wall 150 shown in FIG. 1. The change in the conductive tube overlap area and concomitant change in capacitance change is proportional to the distance that the needle 130 travels. In one embodiment, a desired penetration depth of the needle 130 is the distance that the needle 130 needs to advance in order to reach the blood vessel wall 150.

In one embodiment, the first conductive tube 140 is a thin conductive film (e.g., of a thickness of about 0.001 to 0.005 inches) disposed along the inner diameter of the needle sheath 110. The first conductive tube 140 can be a thin conductive tube that is formed separately from the needle sheath 110 and is inserted into and attached to the needle sheath 110. In one embodiment, the second conductive tube 142 is a thin conductive film (e.g., of a thickness of about 0.001 to 0.005 inches) disposed along the outer diameter of the needle 130. The second conductive tube 142 can be a thin conductive tube that is formed separately from the needle 130 wherein the needle 130 is inserted into the second conductive tube 142.

Typically, the needle 130 is made of a conductive material such as stainless steel or nitinol. When the needle 130 is conductive, the needle 130 is first coated with an insulation film 138 before the second conductive tube 142 is disposed on the needle 130. The needle insulation film 138 may be a tube that is attached to the outer diameter of the needle (needle insulation tube 138). The needle insulation film 138 can be made of a polymeric material or other non-conductive materials.

In one embodiment, the first conductive tube 140 has a length 139 that is about equal to a length 137 of the second conductive tube 142. In one embodiment, the length 139 only extends along a portion of the needle sheath 110 and the length 137 only extends along a portion of the needle 130 and not the entire lengths of these elements (see FIG. 3). In another embodiment, the needle insulation tube 138 may have the same length as one of the length 137 or the length 139. In one embodiment the needle insulation tube 138 may be the same length as the needle 130. In one embodiment, the lengths 137 and 139 are about the length of the penetration depth or the travel distance that the needle 130 needs to penetrate or travel in order to reach a target site. In one embodiment, the lengths 137 and 139 are between about 0.5 mm and about 10 mm.

In one embodiment, the dielectric tube 141 is made out of polymeric material. In another embodiment, the dielectric tube 141 is made out of other non-conductive materials. In one embodiment, the dielectric tube 141 has a length that is equal to the length 137 or the length 139 (e.g., between 0.5–10 mm). In one embodiment the dielectric tube 141 may be the same length as the needle 130. The dielectric tube 141 has a length that is sufficient to insulate the first conductive tube 140 from the second conductive tube 142.

In one embodiment, the delivery catheter 100 includes a ring 134 as illustrated in FIG. 3. The ring 134 is inserted within a proximal end 160 of the needle sheath 110. The ring 134 has an inlet 135. The outer diameter of the ring 134 is slightly smaller than or approximately equal to the inner diameter of the needle sheath 110 at the proximal end 160 so that the ring 134 can fit snuggly within and be fixed to the proximal end 160 of the needle sheath 110. The inlet 135 has a diameter similar to the outer diameter of the needle 130 so that the needle 130 can fit through the inlet 135. A mating set of screw threads is provided between the needle 130 and the inlet 135. The inlet 135 may have a threaded surface and the needle 130 also has a threaded portion 144 at the proximal end of the needle 130. The needle 130 is inserted through the inlet 135. As the needle 130 is turned, the needle 130 is threaded through the ring 134. In one embodiment, the threaded portion 144 allows an operator to control the advancement of the needle 130 through the application of torque at the portion 144 of the needle 130. The needle 130 is advanced in a slow, controlled manner by applying torque at the proximal end 160 of the needle 130. In one embodiment, the ring 134 is made out of a biocompatible polymeric material.

In another embodiment, another ring, ring 136 is included and is inserted at a distal end 162 of the needle sheath 110 as illustrated in FIG. 3. The ring 136 can also be made out of a biocompatible material such as a polymer. The ring 136 has an inlet 137 that has a diameter similar to the outer diameter of the needle 130. The ring 136 is similar to the ring 134. The ring 136 stabilizes and supports the needle 130 within the needle sheath 110, for example, by stabilizing the needle 130 at the center of the needle sheath 110.

FIG. 4 illustrates a cross-sectional view of the delivery catheter 100 that includes the capacitor 101 described above. The first conductive tube 140 is deposited directly on the inner diameter of the needle sheath 110. The dielectric tube 141 is disposed within the first conductive tube 140. The dielectric tube 141 need not be disposed immediately or directly adjacent to the first conductive tube 140. An air gap may exist between the dielectric tube 141 and the first conductive tube 140. The needle 130 includes the needle insulation layer 138, which separates its outer surface from the second conductive tube 142. The second conductive tube 142 is deposited directly onto the outer surface of the needle insulation tube 138.

In one embodiment, when the needle 130 is advanced or retracted within the needle sheath 110, the area of overlap between the first conductive tube 140 and the second conductive tube 142 changes. Changing the overlapping area changes the capacitance. The capacitance change is proportional to the distance that the needle 130 is advanced or retracted within the needle sheath 110. Based on the capacitance change, the distance traveled or penetrated by the needle 130 can be determined. Thus, the capacitor 101 enables an operator (e.g., a clinician, a nurse, or a physician) to accurately determine when the needle tip 132 contacts, reaches, or penetrates, an organ, a cavity wall, a vessel wall, or any other bodily tissue of a patient.

In one embodiment, when the entire length of the first conductive tube 140 and the entire length of the second conductive tube 142 overlap, the capacitance is at maximum. When the needle 130 is advanced or retracted, the second conductive tube 142 slides away from the first conductive tube 140 reducing the area of overlap. The capacitance is proportionally decreased. When the needle 130 is advanced toward a target site, the capacitance change indicates how far the needle 130 has protruded outside the needle sheath 110. The distance traveled by the needle 130 or the distance of protrusion by the needle 130 may indicate a penetration depth that the needle 130 has reached. In one embodiment, the penetration depth of the needle 130 is between 0.5–10 millimeters (mm).

In one embodiment, the capacitor 101 uses air as the dielectric layer 141. In another embodiment, the capacitor 101 uses a fluid as the dielectric layer 141. The capacitor 101 would comprise a first conductive tube 140, a second conductive tube 142, and an air gap 141 (or a fluid path 141) as the dielectric layer 141 as illustrated in FIGS. 3 and 4.

In another embodiment, the components of the capacitor 101 are dimensioned closely to each other. In this embodiment, the first conductive tube 140 is a thin conductive film or tube that is disposed along the inner diameter of the needle sheath 110. The first conductive tube 140 outer diameter is in immediate contact with the inner diameter of the needle sheath 110. The dielectric tube 141 is disposed within the first conductive tube 140. The outer diameter of the dielectric tube 141 is similar to the inner diameter of the first conductive tube 140 such that the dielectric tube 141 is in immediate contact with the inner diameter of the first conductive tube 140.

The needle insulation tube 138 is disposed on the outer diameter of the needle 130. The inner diameter of the needle insulation tube 138 is similar to the outer diameter of the needle 130 such that the needle insulation tube 138 is in immediate contact with the outer diameter of the needle 130. The second conductive tube 142 is disposed immediately on the outer diameter of the needle insulation tube 138. The needle 130 with the needle insulation tube 138 and the second conductive tube 142 is disposed within the inner diameter of the dielectric tube 141. The outer diameter of the second conductive tube 142 is similar to the inner diameter of the dielectric tube 141 such that the outer diameter of the second conductive tube 142 is in immediate contact with the inner diameter of the dielectric tube 141.

In one embodiment the dielectric tube 141 is attached to the first conductive tube 140. In one embodiment the dielectric tube 141 is attached to the second conductive tube 142.

In one embodiment the dielectric tube 141 is not attached to either conductive tube 140 or 142. The dielectric tube 141 cannot be attached to both conductive tubes 140 and 142 simultaneously.

In one embodiment, the dielectric tube 141 also supports the needle 130 such that no ring (e.g., the ring 136) is needed to stabilize or support the needle 130 at the center of the needle sheath 110. The needle 130 is stabilized and supported within the needle sheath 110 because of the close fitting of the first conductive tube 140, the dielectric tube 141, the second conductive tube 142, the needle insulation tube 138, and the needle 130.

In one embodiment, a capacitor 111 is incorporated into the delivery catheter 100 as illustrated in FIGS. 5 and 6. The capacitor 111 is similar to the capacitor 101 discussed in FIG. 3 except that portion of a needle 130 is used as the second conductive tube. In this embodiment, the delivery catheter 100 comprises a first conductive tube 140, a dielectric tube 141, and the needle 130. A second conductive tube is not included. In this embodiment, the first conductive tube 140 and the needle 130 are made out of conductive materials such as aluminum, gold, silver, copper, stainless steel, nitinol, or conductive polymer to name a few. The first conductive tube 140 and the needle 130 make up the two conductive regions needed for the capacitor 111. The first conductive tube 140 and the needle 130 are oppositely charged. For example, the first conductive tube 140 may be positively charged and the needle 130 may be negatively charged. The dielectric tube 141 is disposed to the outer diameter of the needle 130.

In one embodiment, the first conductive tube 140 is a thin film (that is conductive) disposed along the inner diameter of the needle sheath 110. The needle 130 includes a needle insulation layer 131 disposed along the outer diameter of the needle 130 at portions 135 and not portion 133, which is used to form the second conductive region of the capacitor 111. As illustrated in FIG. 5, the needle insulation layer 131 is disposed along the needle 130 at the portions 135. A portion 133 of the needle 130 is not coated with the needle insulation layer 131. The portion 133 and the first conductive tube 140 form the two conductive regions needed for the capacitor 111. The needle insulation layer 131 is made out of a non-conductive material that insulates the portions 135 of the needle 130 that is not used as part of the capacitor 111.

In one embodiment, the first conductive tube 140 has a length 139. The uninsulated portion of the needle 133 has a length 137 shown. The lengths 137 and 139 may be approximately equal to or slightly larger than the penetration depth that the needle 130 needs to travel or penetrate to reach the target site (e.g., 0.5–10 mm). When the first conductive tube 140 and the needle uninsulated portion of the needle 133 overlap at these two lengths (139 and 137), the capacitance is at a maximum value. In one embodiment, as the needle 130 is advanced or retracted within the needle sheath 110, the capacitance between the first conductive tube 140 and the portion 133 of the needle tube 130 changes. In one embodiment, the change in capacitance is proportional to the distance advanced by the needle 130. The distance traveled by the needle 130 may be the penetration depth that the needle 130 needs to penetrate to reach the target site. In one embodiment, the penetration depth of the needle 130 is between about 0.5 and about 10 mm.

Continuing with FIG. 5, in one embodiment, a ring 134 is disposed within the needle sheath 110. The ring 134 is inserted within a proximal end 160 of the needle sheath 110. The needle 130 is inserted through the inlet 135 of the ring 134. As the needle 130 is turned, the needle 130 is threaded through the ring 134. The threaded portion 144 of the needle 130 allows an operator to control the advancement of the needle 130 through the application of torque at the portion 144 of the needle 130.

In another embodiment, another ring (not shown) such as the ring 136 described above in FIG. 3 is disposed at the distal end 162 of the needle sheath 110. The ring helps stabilize and support the needle 130 within the needle sheath 110, for example, by maintaining the needle 130 at the center of the needle sheath 110.

Figure 7:
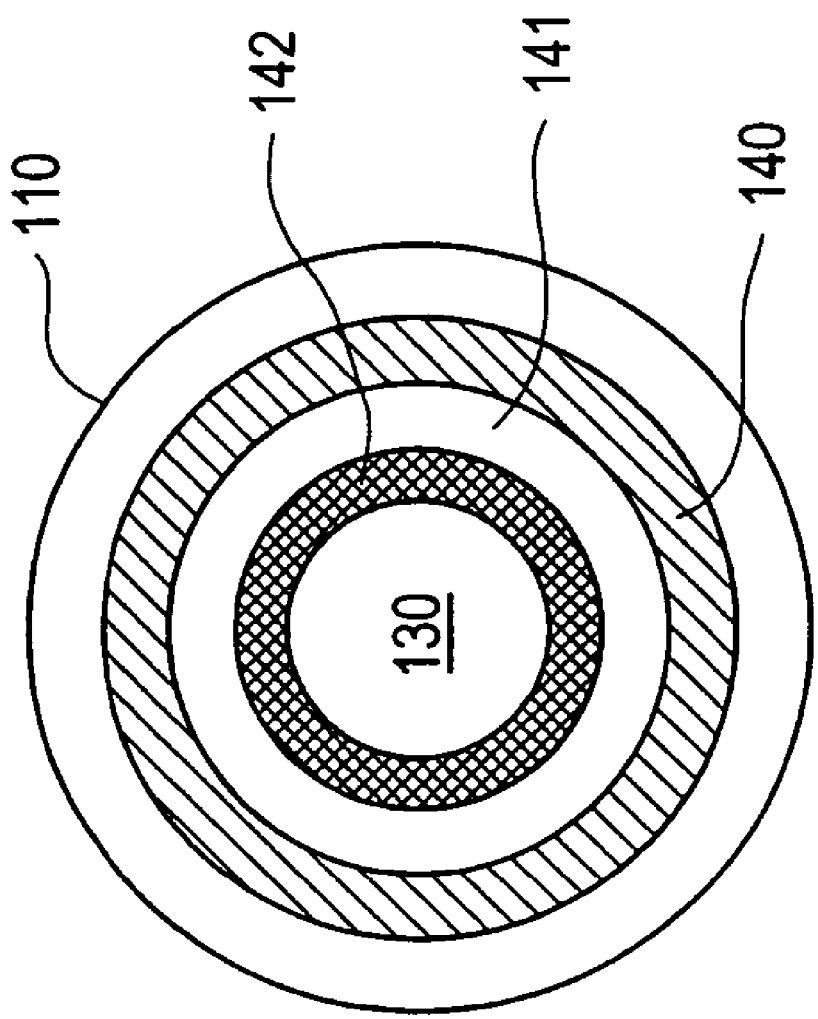
FIG. 7 illustrates a cross-sectional view of another needle assembly with a capacitor wherein the needle is non-conductive.

In an alternative embodiment, the needle 130 is made of non-conductive material such as polymer and silicon. FIG. 7 illustrates a cross section of an exemplary embodiment of a capacitor that can be incorporated into a delivery catheter such as the delivery catheter 100 shown in FIG. 1. This embodiment is similar to the embodiment described in FIG. 3 except that no needle insulation layer 138 is disposed on the outer diameter of the needle 130. As illustrated in FIG. 7, the needle sheath 110 includes the first conductive tube 140 disposed on the inner diameter of the needle sheath 110. The needle 130 includes the second conductive tube 142 disposed on the outer diameter of the needle sheath 110. The dielectric tube 141 separates the first conductive tube 140 and the second conductive tube 142. The dielectric tube 141 can be made of a non-conductive material. The dielectric tube 141 can be an air gap or a fluid path, both of which can function as a dielectric layer that insulate and separate the first conductive tube 140 from the second conductive tube 142. All other aspects of this embodiment are similar to the capacitor 101 illustrated in FIG. 3.

Figure 8:
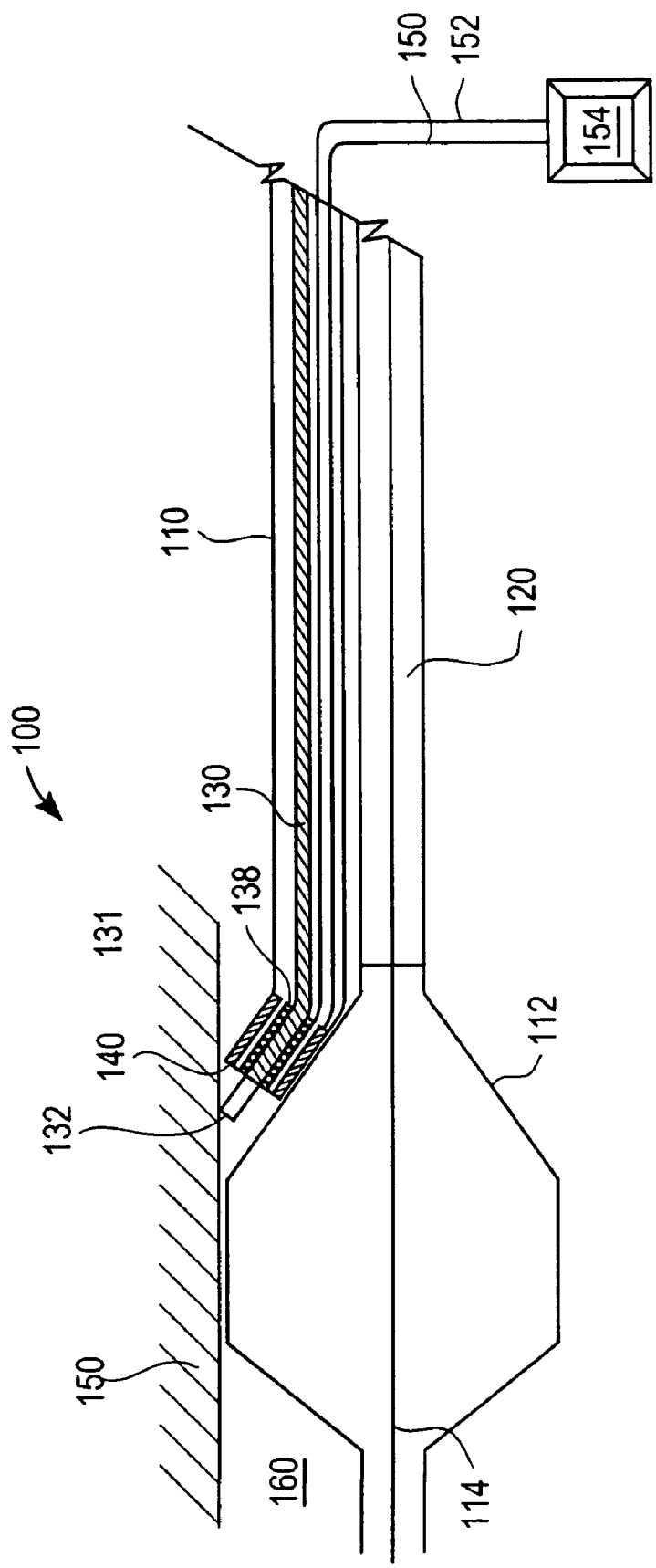
FIG. 8 illustrates an exemplary needle assembly with a capacitor and a capacitance sensor device coupled thereto.

FIG. 8 illustrates an exemplary embodiment of the delivery catheter 100 having a capacitor and a sensor, which are used to determine the distance traveled by the needle 130 included therein. The capacitor can be any of the exemplary capacitors described above (e.g., the capacitor 101 and 111). In one embodiment, the delivery catheter 100 includes a first lead 150, which is coupled to the first conductive tube 140, and a second lead 152, which is coupled to the second conductive tube 142. In another embodiment, the first lead 150 is coupled to the first conductive tube 140 and the second lead 152 is coupled to the needle 130 (that is made out of a conductive material). In another embodiment, the needle 130 can be used as the second lead in the embodiments where the needle 130 itself is conductive. The first lead 150 and the second lead 152 are further coupled to a device 154 that measures and displays the capacitance values obtained for the capacitor in the delivery catheter 100.

In one embodiment, as the needle 130 is advanced or retracted (e.g., as the operator advances or retracts the needle 130 with the balloon 112 inflated) within the needle sheath 110, the capacitance between the first conductive tube 140 and the second conductive tube 142 changes. In another embodiment, as the needle 130 is advanced or retracted within the needle sheath 110, the capacitance between the first conductive tube 140 and the exposed portion of the conductive needle 130 changes. The capacitance is obtained and displayed on the device 154. In one embodiment, the capacitance is proportional to the distance advanced by the needle 130. In one embodiment, this distance indicates the penetration depth of the needle 130.

FIGS. 9 and 10 illustrate the delivery catheter 100, which includes any of the capacitors described above, in different positions with respect to the vessel wall 150. In one embodiment, the vessel wall 150 is the target site. FIG. 9 illustrates the delivery catheter 100 where the needle 130 has not yet contacted the vessel wall 150. The needle tip 132 is close to and proximate to but not contacting the vessel wall 150. In one embodiment, the balloon of the delivery catheter 100 is not yet inflated at this point. The needle sheath 110 is not bent to direct the needle 130 toward the vessel wall 150. In this embodiment, the first conductive tube 140 and the second conductive tube 142 have the maximum overlapping area when the needle 130 has not yet contacted the vessel wall 150. The letter "A" in FIG. 9 indicates the areas of overlap. Alternatively, when the exposed portion of the needle 130 is used as the second conductive tube, the overlapping area "A" indicates the area where the first conductive tube and the exposed portion of the conductive needle overlap.

In one embodiment, the first conductive tube 140 and the second conductive tube 142 have similar length and when they overlap, the entire length of tube 140 overlaps with the entire length of tube 142. An initial capacitance ($C_i$) is measured when the first conductive tube 140 and the second conductive tube 142 overlap by the area "A." As the needle 130 is advanced or retracted within the inner lumen of the needle sheath 110, the capacitance Ci changes as the second conductive tube 142 slides apart from the first conductive tube 140

For instance, as shown in FIG. 10, a portion of the needle tip 132 is contacting and has become embedded in the vessel wall 150 (e.g., as the balloon is dilated bending the needle sheath 110 toward the vessel wall 150). The needle 130 advances a distance "D" as compared to FIG. 9. The area of overlapping "A" is decreased to an overlapping area "A–D" since the needle 130 is advanced by the distance "D." A capacitance $C_2$ is measured when the first conductive tube 140 and the second conductive tube 142 overlap by the area "A–D". The capacitance $C_2$ is compared to the capacitance $C_i$ to give a change in capacitance, which is proportional to the distance "D."

In one embodiment, the needle 130 is inserted to a predetermined penetration depth into the vessel wall 150 (e.g., 0.5–10 mm). The predetermined penetration depth may be equated to the distance "D" illustrated in FIG. 9. In one embodiment, as the needle 130 is advanced, capacitance is continuously measured and displayed by the device 154. A calculation may be performed to determine the amount of needle advancement. When the capacitance displacement is equal to or proportional to the distance "D," the operator advancing the needle 130 into the patient knows that the needle 130 has reached the predetermined penetration depth "D." The needle advancement can then be stopped.

Figure 11:
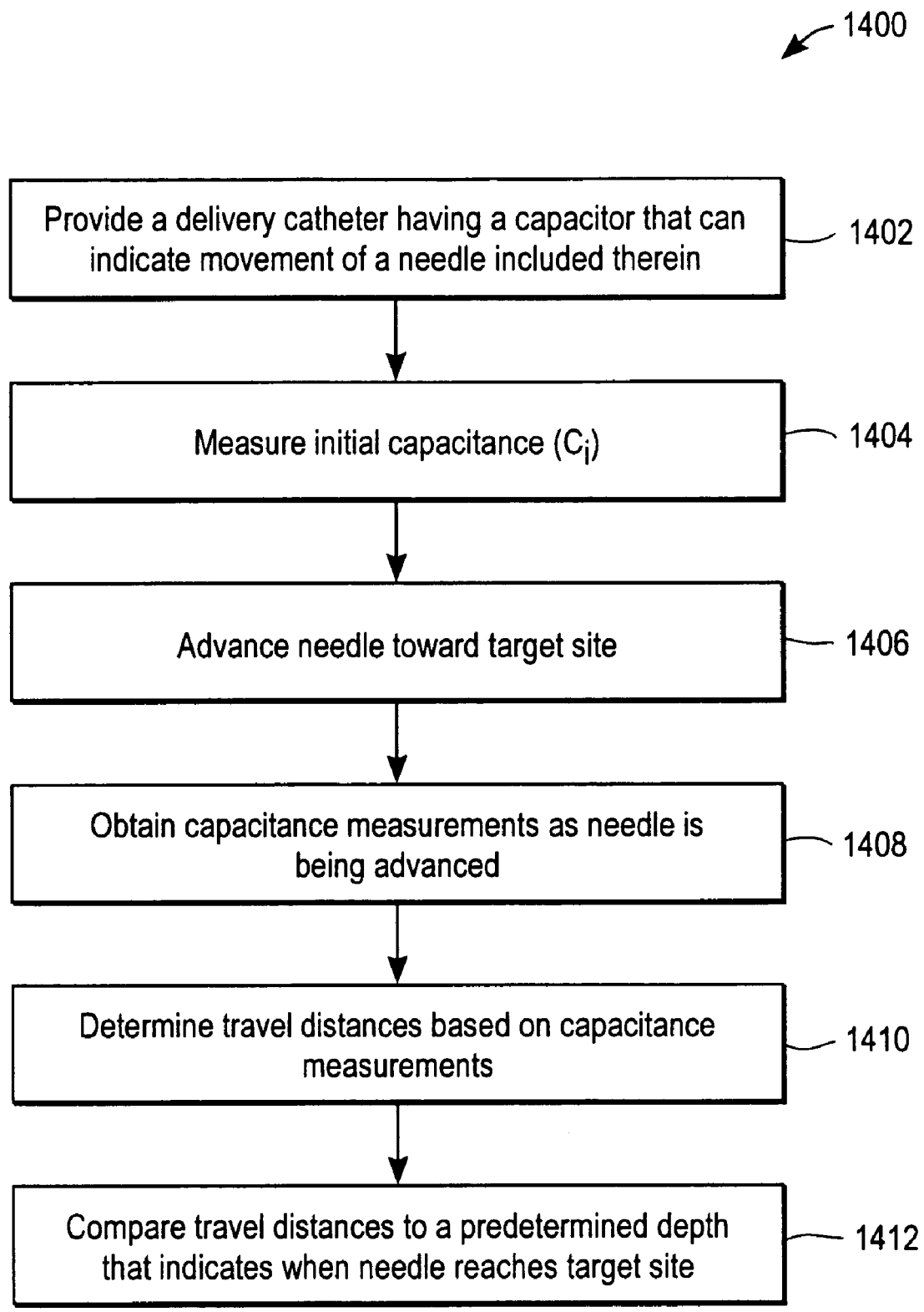
FIG. 11 illustrates a flow diagram of one embodiment of a method for detecting tissue contact and needle penetration depth.

FIG. 11 illustrates the flow chart of one embodiment of a process 1400 of detecting tissue contact and needle penetration depth using the delivery catheter 100 described above. At processing block 1402, a delivery catheter having a capacitor that can indicate movement of a needle included within the delivery catheter is provided. In one embodiment, the delivery catheter is the delivery catheter 100 that includes any of the capacitors previously described above. At processing block 1404, an initial capacitance $C_i$ is measured where the first conductive tube 140 and the second conductive tube 142 have the maximum overlapping area. At processing block 1406, the needle 130 is advanced toward a target site, for example, the vessel wall 150. While the needle 130 is being advanced, capacitance measurements between the first conductive tube 140 and the second conductive tube 142 are obtained as illustrated at processing block 1408. At processing block 1410, the travel distances of the needle is determined based on the capacitance measurements. In one embodiment, as the needle 130 is being advanced, the capacitance measurements are continuously obtained. The capacitance measurements are then used to determine the travel distances by the needle 130. At processing block 1412, the travel distances are compared to a predetermined depth (or a predetermined travel distance) that indicates when the needle reaches the target site. In one embodiment, the capacitance measurements are compared to a capacitance value that would be obtained when the needle 130 reaches a predetermined depth or travels a predetermined distance. This predetermined depth or the predetermined distance may indicate when the needle 130 has reached the target site.

In one embodiment, needle advancement values are calculated based on changes in capacitance. The capacitance values are measured based on the initial capacitance $C_i$ and capacitance values $C_1$ to $C_{1+n}$ that are obtained as the needle 130 is being advanced. The capacitance values are continuously measured to determine the distance advanced by the needle 130. As previously discussed, the capacitance is proportional to the change in the area of overlap of the first conductive tube 140 and the second conductive tube 142. In one embodiment, the change in the area of overlap of the first conductive tube and the second conductive tube indicates the distance advanced by the needle 130. The distance advanced by the needle 130 is continuously compared to a desired needle penetration depth. The advancement of the needle 130 is stopped when the capacitance value indicates that the distance advanced by the needle 130 is equal to the desired needle penetration depth. This indicates that the needle 130 has reached the desired depth at the target site.

Figure 12:
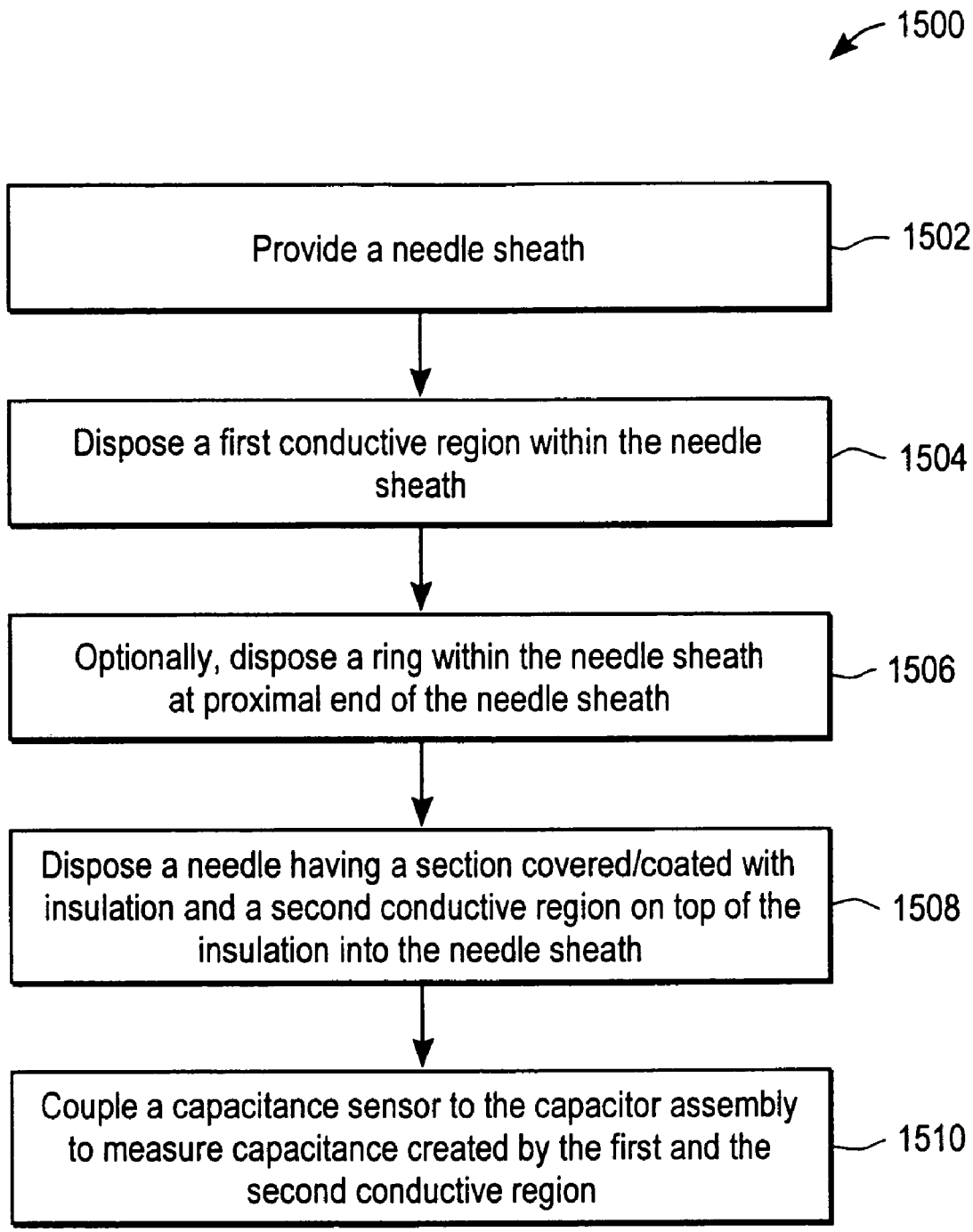
FIG. 12 illustrates an exemplary method of making a needle assembly with a capacitor.

FIG. 12 illustrates an exemplary method 1500 of making a delivery catheter 100 that includes a capacitor in accordance with the present invention. At processing block 1502, a needle sheath (e.g., the needle sheath 110) is provided. At processing block 1504, a first conductive region (e.g., the first conductive tube 140) is disposed within the needle sheath. In one embodiment, the first conductive region is formed by sputtering or coating a conductive film on the inner diameter of the needle sheath. Alternatively, the first conductive region is formed by electro deposition, a technique well known in the art. The conductive film can be a conductive material such as a conductive polymer or metal (e.g., gold, silver, aluminum). In another embodiment, the first conductive region is a thin conductive tube that is disposed or slip fit into and attached to the needle sheath.

Optionally, rings (e.g., a polymeric ring or the ring 134) are disposed within the needle sheath at the distal and proximal ends of the needle sheath as illustrated at processing block 1506. In one embodiment, the proximal ring has an opening with a grooved or threaded surface through which a needle with a threaded portion is disposed.

At processing block 1508, a needle having a section covered or coated with a needle insulation region (e.g., the needle insulation tube 138) and a second conductive region (e.g., the second conductive tube 142) is disposed through the rings and into the needle sheath. In one embodiment, the needle is disposed into and attached to a preformed second conductive tube, which is then disposed through the ring, and into the needle sheath. In another embodiment, a conductive film is deposited on the outer diameter of the needle. In one embodiment, the needle has a threaded portion wherein the needle is threaded through the proximal ring when the needle is being disposed through the ring.

In the method 1500, an air or fluid gap separates the second conductive region from the first conductive region. The air gap acts as a dielectric region to separate the second conductive region from the first conductive region.

At processing block 1510, a capacitance sensor is coupled to the capacitor assembly to measure capacitance created by the first conductive tube and the second conductive tube. In one embodiment, a first lead is coupled to the first conductive tube and a second lead is coupled to the second conductive tube through the ring. The first lead and the second lead are further connected to a device that can measure the capacitance.

Figure 13:
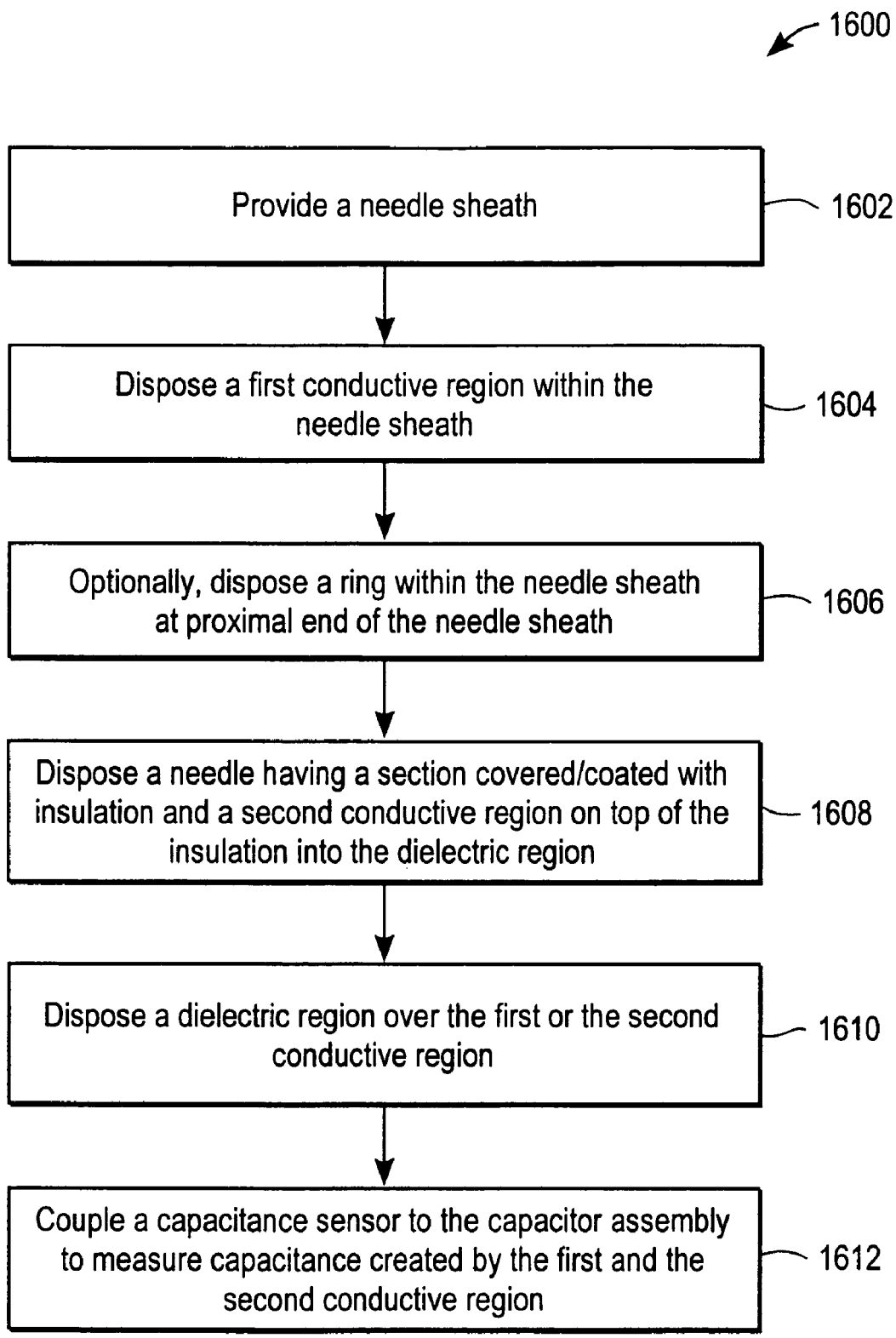
FIG. 13 illustrates another exemplary method of making a needle assembly with a capacitor.

FIG. 13 illustrates another exemplary method 1600 of making a delivery catheter 100 that includes a capacitor in accordance with the present invention. The method 1600 is similar to the method 1500 described in FIG. 15 with an addition of a dielectric region that is not made of air or alternatively, fluid. At processing block 1602, a needle sheath (e.g., the needle sheath 110) is provided. At processing block 1604, a first conductive region (e.g., the first conductive region 140) is disposed within the needle sheath similar to the processing block 1504. Optionally, one or more rings (e.g., the ring 134 and 136) are disposed within the needle sheath at the distal and proximal end of the needle sheath as illustrated at processing block 1606 similar to the processing block 1506. At processing block 1608, a needle having a section covered or coated with a needle insulation region (e.g., the needle insulation tube 138) and a second conductive region (e.g., the second conductive tube 142) is disposed through the ring and into the needle sheath similar to the processing block 1508. At processing block 1610, a dielectric region (e.g., the dielectric tube 141) is disposed over the first or second conductive region. In one embodiment, the dielectric region is slip fitted through the needle sheath that has the first conductive tube. At processing block 1612, a capacitance sensor is coupled to the capacitor assembly to measure capacitance created by the first conductive region and the second conductive region similar to the processing block 1510.

Figure 14:
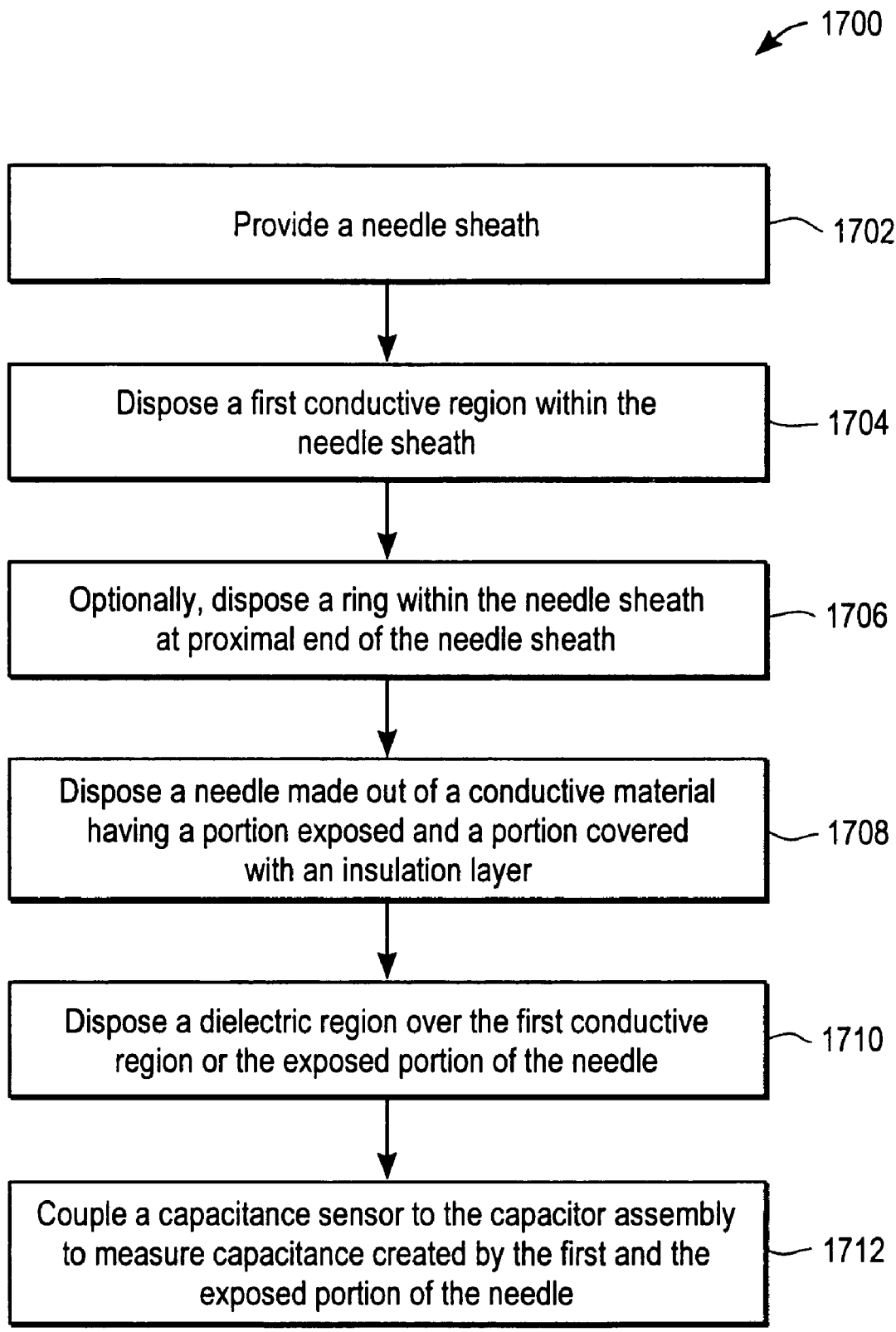
FIG. 14 illustrates yet another exemplary method of making a needle assembly with a capacitor.

FIG. 14 illustrates another exemplary method 1700 of making a delivery catheter 100 that includes a capacitor in accordance with the present invention. The method 1700 is similar to the method 1600 described in FIG. 13 except that the needle is conductive and a portion of the needle is used as the second conductive tube. At processing block 1702, a needle sheath (e.g., the needle sheath 110) is provided. At processing block 1704, a first conductive region (e.g., the first conductive tube) is disposed within the needle sheath similar to the processing block 1504. Optionally, a polymer ring is disposed within the needle sheath at the proximal end of the needle sheath as illustrated at processing block 1706 similar to the processing block 1506. At processing block 1708, a needle made of a conductive material is disposed through the polymer ring and into the dielectric region. The needle has a portion that is to be used as the second conductive tube exposed and the remaining portion of the needled insulated with a needle insulation layer (e.g., the needle insulation tube 135. The exposed portion of the needle acts as the second conductive tube. At processing block 1710, a dielectric region (e.g., the dielectric tube 141) is disposed over the first conductive region or the exposed portion of the needle. In one embodiment, the dielectric region is a tube that is slip fitted through the needle sheath that has the first conductive region. At processing block 1712, a capacitance sensor is coupled to the capacitor assembly to measure capacitance created by the first conductive region and the exposed portion of the needle that acts as the second conductive region similar to the processing block 1510.

Referring back to FIGS. 1–10, note that the first conductive tube 140, the second conductive tube 142, the needle insulation tube 138, and the dielectric tube 141 are, in one exemplary embodiment, tubular in design. The tubular designs enable the needle 130 to rotate within the needle sheath 110 as the needle 130 is being advanced and still have the capacitor 101 surrounding the portion 131 of the delivery catheter. It is envisioned that when the needle 130 is advanced through the needle sheath 110 without being easily rotated, the capacitor 101 need not be in tubular design. The capacitor 101 can have other designs such as a plate design. For instance, a first capacitor plate or a first conductive region is deposited on a portion of the inner diameter of the needle sheath 110. A second capacitor plate or a second conductive region is deposited on a portion of the outer diameter of the insulated needle 130. An insulation layer is deposited on the second capacitor plate. When the needle 130 is advanced or retracted within the needle sheath 110 without being easily rotated, the first capacitor plate and the second capacitor plate are always facing each other with the insulation layer between them to maintain the capacitor. Alternatively, the first conductive tube 140 and the second conductive tube 142 may have slits or holes configured into these regions.

Systems and methods for detecting tissue contact and needle penetration depth have been described. Although the present invention has been described with reference to specific exemplary embodiments, it will be evident that various modifications and changes may be made to these embodiments without departing from the broader spirit and scope of the invention. Accordingly, the specification and drawings are to be regarded in an illustrative rather than a restrictive sense.

What is claimed is:

1. A method of making a capacitor for a delivery catheter comprising:
    providing a needle sheath;
    disposing a first conductive region within said needle sheath;
    disposing a needle having a section covered with a needle insulation layer upon which a second conductive region is disposed within said needle sheath; and
    coupling a capacitance sensor to said needle sheath to measure capacitance created by said first conductive region and said second conductive region.

2. The method of claim 1 further comprising:
    disposing a ring within said needle sheath at a proximal end of said needle sheath wherein said needle is disposed into said needle sheath through said ring.

3. The method of claim 1 further comprising:
    disposing a dielectric region between said first conductive region and said second conductive region.

4. A method of making a capacitor for a delivery catheter comprising:
    providing a needle sheath;
    disposing a first conductive region within said needle sheath;
    disposing a needle made out of a conductive material within said needle sheath, said needle having a first portion covered with an insulation layer and a second portion not covered by said insulation layer; and
    coupling a capacitance sensor to said needle sheath to measure capacitance created by said first conductive region and said second portion of said needle.

5. The method of claim 4 further comprising:
    disposing a ring within said needle sheath at a proximal end of said needle sheath wherein said needle is disposed into said needle sheath through said ring.

6. The method of claim 1 further comprising:
    disposing a dielectric region between said first conductive region and said second portion of said needle.

* * * * *